United States Patent [19]

Towersey et al.

[11] 3,937,693

[45] Feb. 10, 1976

[54] PRODUCTION OF EDIBLE PROTEIN CONTAINING SUBSTANCES

[75] Inventors: Peter John Towersey, High Wycombe; John Longton, Chesham; Geoffrey Norman Cockram, Henley on Thames, all of England

[73] Assignee: Ranks Hovis McDougall Limited, London, England

[22] Filed: Feb. 8, 1974

[21] Appl. No.: 440,775

[30] Foreign Application Priority Data

Feb. 13, 1973 United Kingdom............. 7087/73

[52] U.S. Cl............. 260/112 R; 426/656; 426/425; 195/28 N
[51] Int. Cl.²........................................... A23J 3/00
[58] Field of Search............ 426/62, 148, 204, 364, 426/369, 428, 656, 655; 195/1, 2, 28 R, 104, 28 N; 260/112 R

[56] References Cited

UNITED STATES PATENTS

| | | | |
|---|---|---|---|
| 3,686,144 | 8/1972 | Tamura et al. | 260/112 |
| 3,775,393 | 11/1973 | Akin et al. | 260/112 |
| 3,781,264 | 12/1973 | Akin | 260/112 |

*Primary Examiner*—A. Louis Monacell
*Assistant Examiner*—R. A. Yoncoskie
*Attorney, Agent, or Firm*—Stevens, Davis, Miller & Mosher

[57] ABSTRACT

Process for reducing the nucleic acid content in the production of an edible protein-containing substance comprising contacting a grown non-toxic microfungus of the class Fungi Imperfecti with a solvent comprising between 40% and 100% (by volume) of a lower alkanol containing up to three carbon atoms and thereafter incubating at a pH between 5 and 9.5 and at a temperature between 30°C. and 80°C. for a time of at least 90 seconds.

12 Claims, No Drawings

PRODUCTION OF EDIBLE PROTEIN CONTAINING SUBSTANCES

This invention is for improvements in or relating to the production of edible protein containing substances.

It has particular reference to a process for reducing the nucleic acid content of microfungi.

Our British Specification No. 1,210,356 describes and claims a process for the production of an edible protein-containing substance which comprises incubating and proliferating, under aerobic conditions, an organism which is a non-toxic strain of a microfungus of the class Fungi Imperfecti, in a culture medium containing essential growth-promoting nutrient substances, of which carbon in the form of assimilable carbohydrate constitutes the limiting substrate in proliferation, and separating from the assimilable carbohydrate exhausted medium the proliferated organism which constitutes the edible protein-containing substance.

Our British application No. 8977/70 (Ser. No. 1,331,471) describes and claims a process for the production of an edible protein-containing substance which comprises incubating and proliferating, under aerobic conditions, a non-toxic strain of *Penicillium notatum* or *Penicillium chrysogenum* or a variant or mutant thereof, in a culture medium containing essential growth-promoting nutrient substances, of which carbon in the form of assimilable carbohydrate constitutes the limiting substrate in proliferation, and separating from the assimilable carbohydrate exhausted medium the proliferated organism which constitutes the edible protein-containing substance.

Our Application No. 8978/70 (Serial No. 1,331,472) describes and claims our specific novel strain of *Penicillium notatum-chrysogenum* IMI 138291 and variants and mutants thereof.

Our Application No. 30584/70 and cognate No. 10466/71 (Ser. No. 1,346,062) describes and claims a process for the production of an edible protein-containing substance which comprises incubating and proliferating, under aerobic conditions, a non-toxic strain of the genus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance.

Our Application No. 23452/70 (Ser. No. 1,346,061) describes and claims our specific novel strain of *Fusarium graminearum* Schwabe IMI 145425 and variants and mutants thereof.

The separated proliferated organism comprising the edible protein-containing substance obtained by the fermentation processes of our Applications Nos. 8977/70 (Ser. No. 1,331,471) and 30584/70 and Cognate No. 10466/71 (Ser. No. 1,346,062) may be incorporated into a foodstuff for human or animal consumption.

The processes of our Applications Nos. 8977/70 (Ser. No. 1,331,471) and 30584/70 and Cognate No. 10466/71 (Ser. No. 1,346,062) are capable of producing an edible protein-containing substance comprising fungal mycelium which possesses a high net protein utilisation value on rat assays of at least 70 based on the α-amino nitrogen.

If single-cell protein is to be used as a primary protein source for human consumption the World Health Organisation has advised that the nucleic acid content should be reduced to a level which would allow a maximum intake in the range of 2 grams of nucleic acid per day.

For a processing method to be acceptable, it must not only decrease the nucleic acid level to the required degree, but it also must be inexpensive and must not contaminate the food product with undesirable chemicals.

It is an object of the present invention to provide a process for the reduction of levels of nucleic acid in particular ribonucleic acid (RNA) in proliferated microorganisms combined with the minimum loss of protein to render them more acceptable as human food.

We have developed a process for treating cells of grown non-toxic microfungus of the class Fungi Imperfecti which can meet the above requirements of the World Health Organisation.

The invention provides fungal mycelium possessing a reduced level of RNA of below 4%.

Thus the invention provides fungal mycelium containing *Fusarium graminearum* Schwabe IMI 145425 possessing a reduced level of RNA of below 3% by weight, preferably below 2% by weight.

The invention also provides fungal mycelium containing *Penicillium notatum-chrysogenum* IMI 138291 possessing a reduced level of RNA of below 4%.

According to the present invention there is provided a process for reducing the nucleic acid content in the production of an edible protein-containing substance comprising contacting a grown non-toxic microfungus of the class Fungi Imperfecti with a solvent comprising between 40% and 100% (by volume) of a lower alkanol containing up to three carbon atoms and thereafter incubating at a pH between 5 and 9.5 and at a temperature between 30°C. and 80°C. for a time of at least 90 seconds.

The process may be applied to a grown nontoxic strain of *Fusarium*, *Penicillium notatum* or *Penicillium chrysogenum*, *Penicillium funiculosum* or *Aspergillus niger*.

The strain of Fusarium may be a strain of *Fusarium graminearum* Schwabe in particular IMI 145425, *Fusarium oxysporum* or *Fusarium solani* as described and claimed in our Applications Nos. 23452/70 (Ser. No. 1,346,061) and 30584/70 and Cognate No. 10466/71 (Ser. No. 1,346,062).

The strain of *Penicillium notatum* or *Penicillium chrysogenum* may be a strain of *Penicillium notatum-chrysogenum*, for example IMI 138291, as described and claimed in our Application Nos. 8977/70 (Ser. No. 1,331,471) and 8978/70 (Ser. No. 1,331,472).

The lower alkanol containing up to three carbon atoms may be methyl alcohol, ethyl alcohol, propyl alcohol or isopropyl alcohol. Ethyl alcohol and isopropyl alcohol are solvents permitted by the Solvents in Food Regulations, 1967. The preferred solvent in the process of the present invention is isopropyl alcohol (IPA). Instead of pure isopropyl alcohol aqueous solutions containing between 40 or 50% by volume and up to 100% I.P.A. may be employed.

The incubation may conveniently be carried out at a temperature between 45°C. and 60°C. for a time of between 1.5 minutes and 40 minutes.

The incubation step may conveniently be carried out in the presence of a buffer solution for example NH₄Cl/NH₄OH or NH₄Cl/HCl.

The post fermentation process of the present invention for reducing the nucleic acid content of microorganisms is essentially a two stage process.

STAGE 1

The grown microbial protein or fungal mycelium obtained for example by the fermentation process described and claimed in our Application Nos. 8977/70 (Ser. No. 1,331,471) and 30584/70 and Cognate No. 10466/71 (Ser. No. 1,346,062) may be harvested, filtered to remove growth medium and washed, if desired. It may then be suspended in the alkanol solvent for example for 1 minute at 20°C. or contacted with an alkanol solvent water mixture. The majority or all of the alkanol solvent may be removed by such methods as vacuum filtration, filter pressing or centrifugation. The duration of contact with the alkanol solvent may be varied but is generally in the range between 15 seconds and 15 minutes. The temperature may vary between 0°C. and 60°C.

STAGE 2

The cells may then be brought into intimate contact with aqueous buffer solutions in the pH range 5 to 9.5. Thus the solvent treated cells may then be resuspended and incubated in aqueous buffer solution at pH 8.6 and temperature 45°C. An example of a suitable buffer solution is 0.1 M ammonium chloride solution with ammonium hydroxide added to adjust the pH to 8.6.

The resulting treated cells may then be harvested again for example by filtration and washing with water and thereafter formulated into foods or dried by various methods.

When the process is carried out in the pilotplant the pH is adjusted to 5 after RNA removal. The purpose of this acidification is twofold (a) the material becomes "whiter" and (b) the texture changes and this enables harvesting by vacuum filtration to be carried out easier.

The resulting solvent treated microbial protein or fungal mycelium may have a RNA content of 1–4% compared to 7 to 10% of the untreated proliferated organism.

The cells may be analysed to determine their chemical composition and to evaluate the efficiency of the nucleic acid reduction process.

Following is a description by way of example of methods of carrying the invention into effect.

References to "Biomass Loss" denote weight lost during processing.

Ribonucleic acid (RNA) content was determined by a modification of the method of Schmidt G. and Thannhauser, S. J., J. Biol. Chem., 1945, 161, 83.

Method of analysis for Total Nitrogen (TN) Automatic Kjeldahl digestor (Technicon). A. Ferrari, Ann. N.Y. Sci. 87, 792 (1960).

Amino nitrogen (AN) TNBS (modified). M. A. Pinnegar, Technicon Symposium 1965, p. 80.

EXAMPLE A

Reduction of the Nucleic Acid Levels in Various Micro-Organisms

*Fusarium graminearum* IMI 145425 was cultivated by the following procedure:

Medium in distilled water:

| | | |
|---|---|---|
| K₂HPO₄ | 15.05 | gL⁻¹ |
| (NH₄)₂HPO₄ | 6.64 | gL⁻¹ |
| tri Sodium Citrate | 15.7 | gL⁻¹ |
| Citric Acid | 5.48 | gL⁻¹ |
| K₂SO₄ | 1.0 | gL⁻¹ |
| Choline chloride | 50 | mgL⁻¹ |
| Biotin | 50 | μgL⁻¹ |
| Glucose | 30 | gL⁻¹ |
| Minimal Salts | | |
| MgCl₂.6H₂O | 0.2 | gL⁻¹ |
| ZnSO₄ | 0.003 | gL⁻¹ |
| MnCl₂4H₂O | 0.005 | gL⁻¹ |
| FeCl₃.6H₂O | 0.01 | gL⁻¹ |
| CuCl₂.6H₂O | 0.001 | gL⁻¹ |
| NaMoO₄.2H₂O | 0.001 | gL⁻¹ |
| CoCl₂.6H₂O | 0.001 | gL⁻¹ |
| CaCl₂.2H₂O | 0.015 | gL⁻¹ |

STERILISATION

All components with the exception of glucose are sterilised together, and the amounts of these materials required for 1 liter of medium are dissolved, made up to 850 ml. and distributed into 5 1 liter conical flasks, each containing 170 ml. A 30% w/v solution of glucose is prepared and sterilised in 20 ml. portions in universal bottles. Sterilisation is effected in an autoclave at 15 p.s.i. for 15 minutes.

GROWTH CONDITIONS

Before inoculation with 10 ml. of a growing culture, the contents of one bottle of sterile glucose solution is added to each flask. Culture of A3/5 then proceeds on an Orbital Shaker, with 2 inch throw, at 160 r.p.m. and a temperature of 30°C. The culture is harvested after 18 hours.

Cells were collected and washed on a Buchner filtration system and treated as follows:

i. Suspended in 66% v/v isopropyl alcohol for 1 minute at 20°C.
ii. Isopropyl alcohol was removed by filtration.
iii. The treated cells were incubated in 0.1M NH₄Cl/NH₄OH buffer at pH 8.6 and 45°C. for various times. The incubations were carried out at a slurry concentration of approximately 10 g/l with stirring.

Results

| Micro-fungi | Treatment | Time of Incubation Minutes | % RNA Content | % Amino Nitrogen | % Total Nitrogen |
|---|---|---|---|---|---|
| F. graminearum | None | None | 10.86 | 7.57 | 9.80 |
| | Nucleic acid Reduction | Zero | 9.86 | 8.23 | 10.98 |
| " | | 20 | 2.29 | 8.84 | 10.45 |
| " | | 40 | 1.88 | 8.68 | 9.91 |
| " | | 60 | 1.69 | 8.73 | 10.56 |

CONCLUSION

The level of nucleic acid was effectively reduced by the treatment described.

*Penicillium notatum chrysogenum* IMI 138291 was cultivated by the following procedure:

MEDIUM

2% Soluble starch
0.2% Spray dried corn steep liquor 0.2% Mycological peptone
0.4% $(NH_4)_2SO_4$
0.2% $KH_2PO_4$
1% Sucrose The medium is made up with hot tap water, and dispensed in 200 ml. aliquots into conical shake flasks.

0.1 ml. of liquid amylase was added to each shake flask and incubated at 70°C. for 15 minutes so that the starch was broken down and the viscosity reduced.

STERILISATION

The flasks were sterilised in an autoclave at 15 p.s.i. for 20 minutes.

GROWTH CONDITIONS

A spore inoculum was added to each flask and the culture grown at 30°C. on an orbital shaker with a 2 inch throw at 160 r.p.m. After growth for 24 hours, 10 ml. of the growing culture was used as growing inoculum which was added to more flasks containing the starch medium. Cells produced after a further 24 hours growth were harvested, washed and used as follows:

i. Suspended in 66% (v/v) isopropyl alcohol for one minute at 20°C.
ii. Isopropyl alcohol was removed by filtration.
iii. The treated cells were incubated in 0.1M $NH_4Cl/NH_4OH$ buffer at pH 8.6 and 40°C. for various times. The incubations were carried out at a slurry concentration of approximately 10 gm/l with stirring.

| Results Micro-fungi | Treatment | Time of Incubation Minutes | % RNA content | % Amino Nitrogen | % Total Nitrogen | % Biomass Loss |
|---|---|---|---|---|---|---|
| P. notatum-chrysogenum | None | None | 7.19 | 5.78 | 7.58 | 0 |
| " | Nucleic Acid Reduction | 15 | 3.60 | 6.64 | 8.47 | 30 |
| " | " | 40 | 3.25 | 6.47 | 8.52 | 32 |
| " | " | 60 | 3.32 | 6.34 | 8.04 | 32 |

CONCLUSION

The level of nucleic acid was reduced by the treatment described.

*Penicillium funiculosum* IMI 79195 was cultivated by the following procedure:

| Medium | | |
|---|---|---|
| $KH_2PO_4$ | 15 g/l | |
| NaOH | 1 g/l | |
| Dextran | 1 g/l | |
| Caster Oil | 10 g/l | |
| Solution A+ | 5 ml/l | |
| Solution B+ | 5 ml/l | |
| Solution C+ | 5 ml/l | |
| Yeast extract | 10 g/l | |

Minimal salts

| A+ | | B+ | | C+ | |
|---|---|---|---|---|---|
| $MgSO_4$ | 50 | $CaCl_2$ 3 g/l | $FeSO_4$ | 1 g/l | |
| $ZnSO_4$ | 1 g/l | | | | |
| $MnSO_4$ | 1 g/l | $CoCl_2$ 0.2 g/l | | | |
| $CuSO_4$ | 0.2 g/l | | | | |

All in distilled water.

STERILISATION

Adjust pH of medium to 5.5 before sterilisation. Autoclave all components together. (50 minutes 15 p.s.i.)

GROWTH CONDITIONS (Batch culture)    Volume 10l. (Fermenter)
Temperature 28°C.
Stirrer 400 r.p.m.
Air flow 10l/minutes
Harvest time 80 hours
Inoculum size 5% by volume
(shake flask culture)

Cells were collected and washed on a Buchner filtration system and treated as follows:

i. Suspended in 80% isopropyl alcohol for 1 minute at 20°C.
ii. Isopropyl alcohol was removed by filtration.
iii. The treated cells were incubated in 0.1M $NH_4Cl/NH_4OH$ buffer at pH 8.6 and 37°C. for 60 minutes. The incubation was carried out at a slurry concentration of approximately 10 g/l with stirring.

| Results Micro-organism | Treatment | % RNA content | % Amine N | % Total N |
|---|---|---|---|---|
| P. funiculosum | None | 4.23 | 3.74 | 5.81 |
| P. funiculosum | Nucleic Acid Reduction | 2.80 | 4.46 | 7.34 |

CONCLUSION

The level of nucleic acid was reduced by the treatment described.

*Aspergillus niger* NRRL 330 was cultivated by the following procedure:

The medium and sterilisation procedure were identical to that described for *P. notatum-chrysogenum*.

Growth conditions were also identical except that cells grown directly from spores were used instead of cells cultivated from growing inoculum.

Cells were collected and washed on a Buchner filtration system and treated as follows:

i. Suspended in 66% (v/v) isopropyl alcohol for 1 minute at 20°C.
ii. Isopropyl alcohol was removed by filtration.
iii. The treated cells were incubated in 0.1M $NH_4Cl/NH_4OH$ buffer at pH 8.6 and 40°C. for various times. The incubations were carried out at a slurry concentration of approximately 10 g/l with stirring.

| Results Micro-fungi | Treatment | Time of Incubation Minutes | % RNA Content | % Amino Nitrogen | % Total Nitrogen | % Biomass loss |
|---|---|---|---|---|---|---|
| A.niger | None | None | 6.36 | 4.03 | 5.70 | none |
| " | Nucleic acid Reduction | zero | | | | |
| " | " | 15 | 1.88 | 4.40 | 6.30 | 27 |
| " | " | 30 | 1.86 | 4.35 | 5.77 | 28 |
| " | " | 60 | 1.82 | 4.25 | 5.62 | 32 |

CONCLUSION

The level of nucleic acid was effectively reduced by the treatment described.

EXAMPLE B

Effect of the % Iso-Propyl Alcohol on the Efficiency of the Nucleic Acid Reduction Process

*F. graminearum* IMI 145425, cultivated as described in Example A, was contacted with various isopropyl alcohol/water mixtures at 20°C. for 2 minutes. The treated cells were then incubated in 0.1M $NH_4Cl/NH_4OH$ buffer pH 8.5 at 37°C. for 20 minutes. The incubations were carried out at a slurry concentration of approximately 10 g/l with stirring.

| Results % IPA (by volume) | Treatment | % Biomass loss | % RNA remaining |
|---|---|---|---|
| 0 | None | 0.0 | 9.33 |
| 0 | Nucleic acid reduction | 1.8 | 9.33 |
| 10 | " | 1.1 | 10.68 |
| 20 | " | 11.3 | 9.74 |
| 30 | " | 19.4 | 8.87 |
| 40 | " | 25.6 | 4.58 |
| 50 | " | 26.5 | 3.03 |
| 60 | " | 28.0 | 3.25 |
| 70 | " | 27.6 | 2.86 |
| 80 | " | 26.3 | 3.35 |
| 90 | " | 23.8 | 3.69 |
| 100 | " | 25.1 | 4.58 |

CONCLUSION

The nucleic acid removal process is most effective in the range of 40–100% isopropyl alcohol.

In the case of the treatment with 10 & 20% IPA the final RNA content is greater than the starting material; this is because RNA is removed to a lesser extent than biomass lost.

EXAMPLE C

Effect of Contact with IPA at Various Temperatures on the Subsequent Nucleic Acid Reduction Process

*F. graminearum* IMI 145425, cultivated as described in Example A, was contacted with 100% IPA at 0°, 20°, 40°, and 60°C. for 2 minutes, then incubated with 0.1M $NH_4Cl/NH_4OH$ buffer pH 8.5 for 20 minutes at 39°C. The incubations were carried out at a slurry concentration of approximately 10 g/l with stirring.

| Results Temperature of IPA treatment | % RNA remaining |
|---|---|
| No treatment | 9.04 |
| 0°C | 3.42 |
| 20°C | 3.47 |
| 40°C | 2.52 |
| 60°C | 2.33 |

CONCLUSION

The nucleic acid reduction process is effective over the temperature range studied.

EXAMPLE D

Effectiveness of Various Alcohols on the Nucleic Acid Reduction Process

*F. graminearum* IMI 145425, cultivated as described in Example A, was contacted with 100% iso-propyl alcohol, 70% iso-propyl alcohol, 70% propyl alcohol, 100% ethyl alcohol or 100% methyl alcohol at 20°C. for two minutes, then incubated with 0.1M $NH_4Cl/NH_4OH$ buffer pH 8.5 at 37°C. or 40°C. for various time periods. The incubations were carried out at a slurry concentration of approximately 10 g/l with stirring.

| Results Alcohol used | | Time and temperature of second incubation | | % RNA remaining |
|---|---|---|---|---|
| None | None | None | | 9.16 |
| 100% | iso-propyl alcohol | 30 | mins. at 37°C | 2.53 |
| 100% | " | 120 | mins. at 37°C | 0.70 |
| 70% | " | 20 | mins. at 40°C | 1.81 |
| 70% | propyl alcohol | 20 | mins. at 40°C | 1.93 |
| 100% | ethyl alcohol | 30 | mins. at 37°C | 2.17 |
| 100% | " | 120 | mins. at 37°C | 0.64 |
| 100% | methyl alcohol | 30 | mins. at 37°C | 5.50 |
| 100% | " | 120 | mins. at 37°C | 1.17 |

CONCLUSION

The RNA reduction process is successfully activated by a lower alkanol containing up to three carbon atoms.

EXAMPLE E

Duration of Contact with Iso-Propyl Alcohol

*F. graminearum* IMI 145425, cultivated as described in Example A, was contacted with 66% (v/v) IPA at 20°C. for various times then incubated in 0.1M $NH_4Cl/NH_4OH$ buffer pH 8.5 at 37°C. for 60 minutes.

The incubations were carried out at a slurry concentration of approximately 10 g/l with stirring.

Results

| Contact time with 66% IPA | % RNA remaining | % Biomass lost |
|---|---|---|
| 0 | 9.25 | 0 |
| 15 seconds | 1.12 | 36 |
| 1 minute | 1.14 | 38 |
| 2 minutes | 0.98 | 40 |
| 5 minutes | 1.23 | — |
| 15 minutes | 1.27 | 41 |

CONCLUSION

Over the contact times studied nucleic acid removal was efficient. In practice the contact time for best RNA reduction is around 2 minutes, at longer contact times the % biomass lost tends to rise to unacceptably high values.

EXAMPLE F

Efficiency of Nucleic Acid Reduction with Buffers over a pH Range of 4–10

*F. graminearum* IMI 145425, cultivated as described in Example A, was contacted with 100% iso-propyl alcohol at 20°C. and incubated with the following series of buffers at 30°C. for 3 hours. The incubations were carried out at a slurry concentration of approximately 10 g/l with stirring.

Results

| Buffer in second stage | | | | | | | | % RNA Remaining |
|---|---|---|---|---|---|---|---|---|
| 0.1 M | $NH_4Cl$ | +HCl | to | bring | to | pH | 4.0 | 11.49 |
| " | " | " | " | " | " | " | 4.5 | 9.07 |
| " | " | " | " | " | " | " | 5.0 | 5.85 |
| " | " | " | " | " | " | " | 5.5 | 3.52 |
| " | " + | $NH_4OH$ | " | " | " | " | 6.0 | 2.63 |
| " | " | " | " | " | " | " | 6.5 | 1.60 |
| " | " | " | " | " | " | " | 7.0 | 0.96 |
| " | " | " | " | " | " | " | 7.5 | 0.97 |
| " | " | " | " | " | " | " | 8.0 | 0.59 |
| " | " | " | " | " | " | " | 8.5 | 0.91 |
| " | " | " | " | " | " | " | 9.0 | 1.69 |
| " | " | " | " | " | " | " | 9.5 | 3.84 |
| " | " | " | " | " | " | " | 10.0 | 7.00 |

CONCLUSION

The nucleic acid removal is effective with this buffer system over the pH range 5–9.5.

EXAMPLE G

Efficiency of Nucleic Acid Reduction Carried out in Buffers of Varying Ionic Strengths

*F. graminearum* IMI 145425 cultivated as described in Example A, was contacted with 66% (v/v) IPA at 20°C. for 1 minute, and incubated in buffers or non-buffered solutions of varying ionic strengths at 45°C. The incubations were carried out at approximately 10 g/l with stirring.

Results

| Buffer system | Treatment | Time of incubation at 45°C (Minutes) | % RNA | % Amino Nitrogen | % Total Nitrogen |
|---|---|---|---|---|---|
| None | None | None | 10.89 | 7.57 | 9.80 |
| | Nucleic acid reduced | 0 | 11.21 | 7.82 | 10.53 |
| Distilled water pH 5.7 | " | 20 | 7.38 | 8.07 | 10.22 |
| | " | 40 | 4.79 | 7.97 | 10.12 |
| | " | 60 | 2.57 | 8.40 | 9.84 |
| Non-buffered ammonia solution sufficient to bring to pH 8.5 | " | 0 | 11.17 | 8.35 | 10.81 |
| | " | 20 | 4.54 | 8.85 | 10.07 |
| | "40 | 3.14 | 8.85 | 10.68 | |
| | " | 60 | 2.55 | 8.79 | 10.30 |
| 0.02 M $NH_4Cl/NH_4OH$ buffer pH 8.5 | " | 0 | 9.96 | 8.46 | 10.89 |
| | " | 20 | 3.21 | 8.62 | 10.38 |
| | " | 40 | 2.39 | 8.73 | 10.36 |
| | " | 60 | 1.82 | 8.90 | 10.12 |
| 0.1M $NH_4Cl/NH_4CH$ buffer pH 8.5 | " | 0 | 9.86 | 8.23 | 10.98 |
| | " | 20 | 2.29 | 8.84 | 10.45 |
| | " | 40 | 1.88 | 8.68 | 9.91 |
| | " | 60 | 1.69 | 8.73 | 10.56 |
| 0.5M $NH_4Cl/NH_4OH$ buffer pH 8.5 | " | 0 | 10.02 | 8.21 | 10.58 |
| | " | 20 | 5.85 | 8.35 | 10.13 |
| | " | 40 | 5.63 | 8.42 | 10.01 |
| | " | 60 | 5.58 | 8.54 | 10.12 |
| 1.0M $NH_4Cl/NH_4OH$ buffer pH 8.5 | " | 0 | 10.19 | 7.56 | 10.89 |
| | " | 20 | 10.45 | 7.72 | 10.48 |
| | " | 40 | 9.96 | 7.99 | 10.81 |
| | " | 60 | 9.89 | 8.15 | 10.58 |

CONCLUSION

Nucleic acid is most effectively reduced at lower ionic strengths. The optimum conditions for rapid reduction being 0.1M buffer.

EXAMPLE H

The Nucleic Acid Reduction Process Studied at Various Temperatures

*F. graminearum* IMI 145425, cultivated as described in Example A, was contacted with 66% (v/v) IPA at 20°C for 2 minutes, and incubated in 0.1M $NH_4Cl/NH_4OH$ buffer pH 8.5 for various durations at various temperatures. The incubations were carried out at approximately 10 g/l with stirring.

Results

| Temperature of buffer | Time of incubation minutes | % RNA remaining |
|---|---|---|
| Control | — | 9.44 |
| 30°C | 0 | 10.83 |
| 30°C | 20 | 8.40 |
| 30°C | 40 | 7.06 |
| 30°C | 60 | 7.45 |
| 30°C | 90 | 4.76 |
| 30°C | 120 | 4.11 |
| 37°C | 0 | 10.12 |
| 37°C | 20 | 5.02 |
| 37°C | 40 | 3.55 |
| 37°C | 60 | — |
| 37°C | 90 | 1.80 |
| 37°C | 120 | 1.02 |
| 45°C | 0 | 10.09 |
| 45°C | 20 | 2.58 |
| 45°C | 40 | 0.99 |
| 45°C | 60 | 0.69 |
| 45°C | 90 | 0.69 |
| 45°C | 120 | 0.61 |
| 55°C | 1.5 | 2.16 |
| 55°C | 3.0 | 1.10 |
| 55°C | 4.5 | 0.76 |
| 60°C | 1.5 | 1.96 |
| 60°C | 3.0 | 1.78 |
| 60°C | 4.5 | 1.11 |
| 70°C | 2.0 | 4.19 |
| 70°C | 3.5 | 3.30 |
| 70°C | 5.0 | 3.56 |
| 80°C | 1.5 | 5.65 |
| 80°C | 3.0 | 5.40 |
| 80°C | 4.5 | 5.31 |

CONCLUSION

Nucleic acid reduction takes place over the temperature range 30°–80°C. The most efficient conditions are at a temperature of 60°C., where satisfactory reduction of RNA was achieved within 90 seconds.

We claim:

1. A process for reducing the nucleic acid content in the production of an edible protein-containing substance comprising contacting a grown non-toxic microfungus of the class Fungi Imperfecti with a solvent comprising between 40% and 100% by volume of a lower alkanol containing up to three carbon atoms and the remainder being water, substantially separating said solvent from said microfungus, incubating said microfungus at a pH between 5 and 9.5 in an aqueous suspension and at a temperature between 30°C and 80°C for a time of at least 90 seconds and thereafter separating said microfungus from the aqueous suspension.

2. A process as claimed in claim 1 wherein the grown non-toxic microfungus of the class Fungi Imperfecti is a grown non-toxic strain of *Fusarium, Penicillium notatum, Penicillium chrysogenum Penicillium tuniculosum* or *Aspergillus niger*.

3. A process as claimed in claim 2 wherein the strain of Fusarium is a strain of *Fusarium graminearum* Schwabe, *Fusarium oxysporum* or *Fusarium solani*.

4. A process as claimed in claim 3 wherein the strain of *Fusarium graminearum* Schwabe is our strain of *Fusarium graminearum* Schwabe deposited with the Commonwealth Mycological Institute and assigned the number IMI 145425.

5. A process as claimed in claim 2 wherein the strain of *Penicillium notatum* or *Penicillium chrysogenum* is our strain of *Penicillium notatum-chrysogenum* deposited with the Commonwealth Mycological Institute and assigned the number IMI 138291.

6. A process as claimed in claim 1 wherein the lower alkanol containing up to three carbon atoms is methyl alcohol, ethyl alcohol or propyl alcohol.

7. A process as claimed in claim 1 wherein the lower alkanol containing up to three carbon atoms is isopropyl alcohol.

8. A process as claimed in claim 7 wherein an aqueous solution containing between 50% and 100% isopropyl alcohol is employed.

9. A process as claimed in claim 1 wherein the incubation is carried out at a temperature between 45° and 60°C.

10. A process as claimed in claim 9 wherein the incubation is carried out for a time of between 1.5 minutes and 40 minutes.

11. A process as claimed in claim 1 wherein the incubation step is carried out in the presence of a buffer solution.

12. A process as claimed in claim 11 wherein the buffer solution is $NH_4Cl/NH_4OH$ or $NH_4Cl/HCl$.

* * * * *